(12) United States Patent
Mitchell

(10) Patent No.: US 10,012,549 B2
(45) Date of Patent: Jul. 3, 2018

(54) DEVICE, SYSTEM AND METHOD FOR DETERMINING THE TEMPERATURE AND ORIENTATION OF A MEDIUM

(71) Applicant: Dennis Alan Mitchell, Huntington, NY (US)

(72) Inventor: Dennis Alan Mitchell, Huntington, NY (US)

( * ) Notice: Subject to any disclaimer, the term of this patent is extended or adjusted under 35 U.S.C. 154(b) by 313 days.

(21) Appl. No.: 14/850,307

(22) Filed: Sep. 10, 2015

(65) Prior Publication Data

US 2016/0069853 A1    Mar. 10, 2016

Related U.S. Application Data

(60) Provisional application No. 62/048,473, filed on Sep. 10, 2014.

(51) Int. Cl.

| | |
|---|---|
| *G01K 1/02* | (2006.01) |
| *A47J 43/28* | (2006.01) |
| *A47J 36/00* | (2006.01) |
| *A47J 37/06* | (2006.01) |
| *A47J 37/07* | (2006.01) |
| *A47J 37/10* | (2006.01) |

(52) U.S. Cl.
CPC ............... *G01K 1/024* (2013.01); *A47J 36/00* (2013.01); *A47J 37/0664* (2013.01); *A47J 37/0786* (2013.01); *A47J 37/108* (2013.01); *A47J 43/28* (2013.01); *A47J 2202/00* (2013.01); *G01K 2207/06* (2013.01)

(58) Field of Classification Search
CPC .................................................. G01K 2207/06

USPC ......................................................... 374/155
See application file for complete search history.

(56) References Cited

U.S. PATENT DOCUMENTS

| | | | |
|---|---|---|---|
| 6,698,923 B2 * | 3/2004 | Bedetti .................... | A47J 43/28 374/149 |
| 7,075,442 B2 * | 7/2006 | Lion ....................... | G01K 1/024 340/540 |
| 7,202,454 B2 * | 4/2007 | Wiedemann ............ | A47J 27/62 219/494 |

(Continued)

FOREIGN PATENT DOCUMENTS

WO    WO 2013082227 A1 *   6/2013   ........... A01K 29/005

OTHER PUBLICATIONS

ISR dated Dec. 18, 2015.

*Primary Examiner* — Clayton E LaBalle
*Assistant Examiner* — Leon W Rhodes, Jr.

(57) ABSTRACT

A device, system and method for remotely determining the temperature and orientation of at least one medium is provided. The device may form a body adapted to penetrate a medium, wherein the body houses a thermal sensor, an accelerometer sensor, a gyroscopic sensor, each electronically connected to a wireless transmitter extending from the body. The plurality of sensors may be adapted to determine the continuous temperature, relative position and orientation of the penetrated medium, all relative to time, while the wireless transmitter is adapted to transmit the plurality such determinations to at least one remote device. The resulting system enables a user to remotely monitoring a level of doneness for a plurality of media in terms of their respective temperatures, orientations, and positioning relative to the time spent on or in at least one heating element.

10 Claims, 3 Drawing Sheets

(56) References Cited

U.S. PATENT DOCUMENTS

| | | | | |
|---|---|---|---|---|
| 8,557,317 B2* | 10/2013 | Sonnendorfer | ........... | F24C 7/08 |
| | | | | 219/494 |
| 2003/0214999 A1 | 11/2003 | Chapman et al. | | |
| 2013/0306626 A1 | 11/2013 | Torres et al. | | |
| 2014/0341254 A1* | 11/2014 | Mendez | ................. | G01K 13/00 |
| | | | | 374/137 |
| 2015/0008216 A1* | 1/2015 | Pippia | ..................... | F24C 7/083 |
| | | | | 219/627 |
| 2015/0208858 A1* | 7/2015 | Robbins | ................ | A47J 45/068 |
| | | | | 426/231 |
| 2016/0051078 A1* | 2/2016 | Jenkins | ................... | A47J 27/62 |
| | | | | 99/331 |

* cited by examiner

DEVICE, SYSTEM AND METHOD FOR DETERMINING THE TEMPERATURE AND ORIENTATION OF A MEDIUM

CROSS-REFERENCE TO RELATED APPLICATION

This application claims the benefit of priority of U.S. provisional application No. 62/048,473, filed 10 Sep. 2014, the contents of which are herein incorporated by reference.

BACKGROUND OF THE INVENTION

The present invention relates to devices, systems and methods for determining the temperature and orientation of a medium and, more particularly, a device, system and method for remotely determining the temperature and orientation of a medium.

Foodstuff temperature sensors, so-called meat thermometers, are well known in the art, and typically involve spearing the foodstuff with a probe configured to determine the interior temperature thereof, whereby said temperature is displayed on the device. As a result, such devices require a user to have visual access to the device, which may necessitate opening and re-opening an underlying cooking apparatus, e.g., the oven door, the lid of a barbeque grill and the like. Excessive opening of the cooking apparatus can have deleterious cooking consequences as well has be inconvenient and invite a burning hazard. Moreover, all such temperature sensors do not incorporate or analyze the orientation of the foodstuff. As a result, information regarding how long the foodstuff has remaining undisturbed, regarding how long the foodstuff has cooked on different sides, regarding how long the foodstuff has cooked in a specific region of the underlying cooking apparatus, and the like is not helpfully provided.

As can be seen, there is a need for a device that remotely determines the temperature and orientation of a medium, such as foodstuff.

SUMMARY OF THE INVENTION

In one aspect of the present invention, device for remotely determining levels of doneness for a medium includes a body housing a thermal sensor and a accelerometer sensor; and a wireless transmitter extending from the body, wherein the wireless transmitter is electronically connected to said sensors so that their determinations are time dependent.

In another aspect of the present invention, a device for remotely determining levels of doneness for a medium includes a body housing a thermal sensor, an accelerometer sensor and a gyroscopic sensor, wherein the body is made of heat resistant material formed into a conical shape at one end; a wireless transmitter electronically connected to said sensors so that their determinations are time dependent; and a bridge interconnecting the wireless transmitter and an end opposing the one end of the body.

In yet another aspect of the present invention, a method for remotely determining a level of doneness of at least one medium includes the steps of: providing a device for remotely determining levels of doneness for a medium having a body housing a thermal sensor and an accelerometer sensor; and a wireless transmitter extending from one end of the body, wherein the wireless transmitter is electronically connected to said sensors so that their determinations are time dependent; providing a remote device configured to display output data of said sensors relative to time; penetrating each medium with the device so that the wireless transmitter protrudes from its penetrated medium; and positioning each medium on a heating element.

These and other features, aspects and advantages of the present invention will become better understood with reference to the following drawings, description and claims.

DETAILED DESCRIPTION OF THE INVENTION

Figure 1:
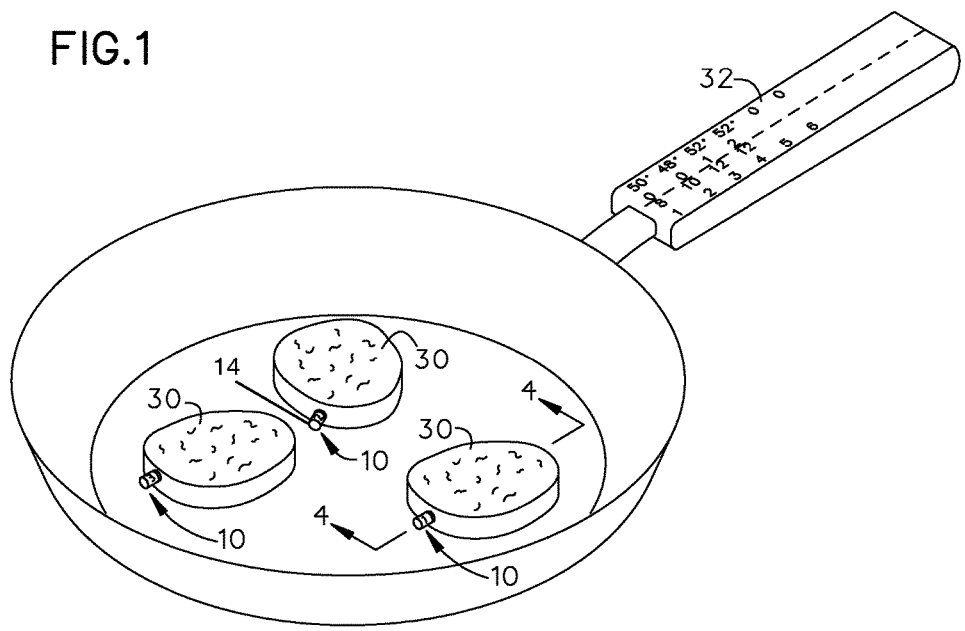
FIG. 1 is a perspective view of an exemplary embodiment of the present invention, illustrated in use.
Figure 2:
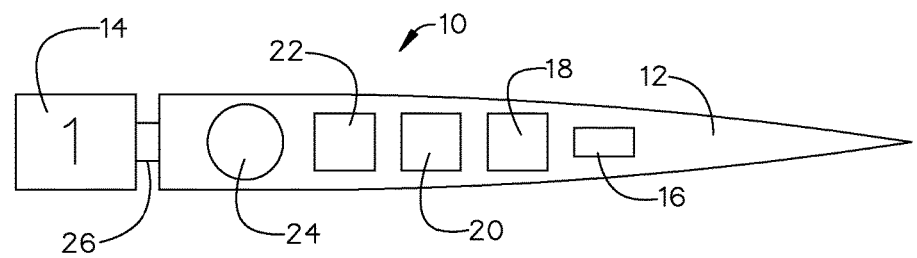
FIG. 2 is a side view of an exemplary embodiment of the present invention.
Figure 3:
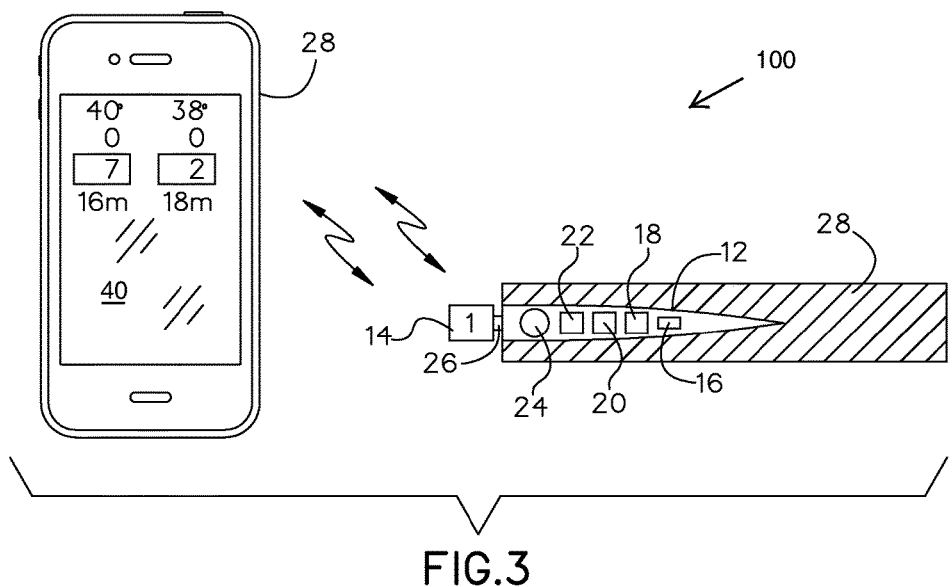
FIG. 3 is a detailed view of an exemplary embodiment of the present invention, illustrating a sensing system.
Figure 4:
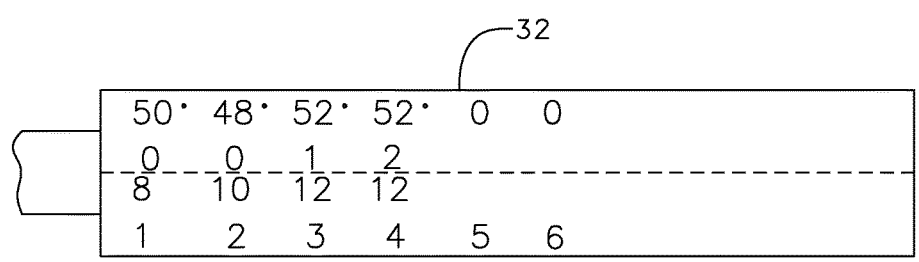
FIG. 4 is a detailed view of an exemplary embodiment of the present invention.
Figure 5:
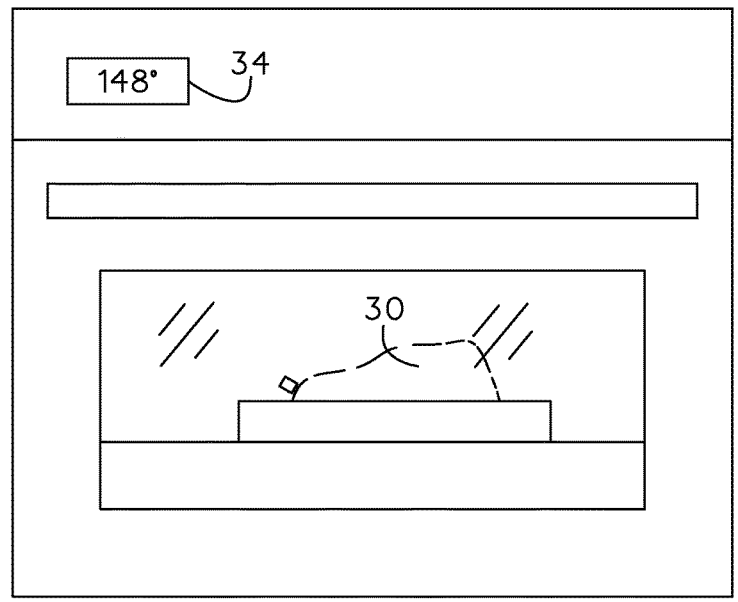
FIG. 5 is a perspective view of an exemplary embodiment of the present invention.
Figure 6:
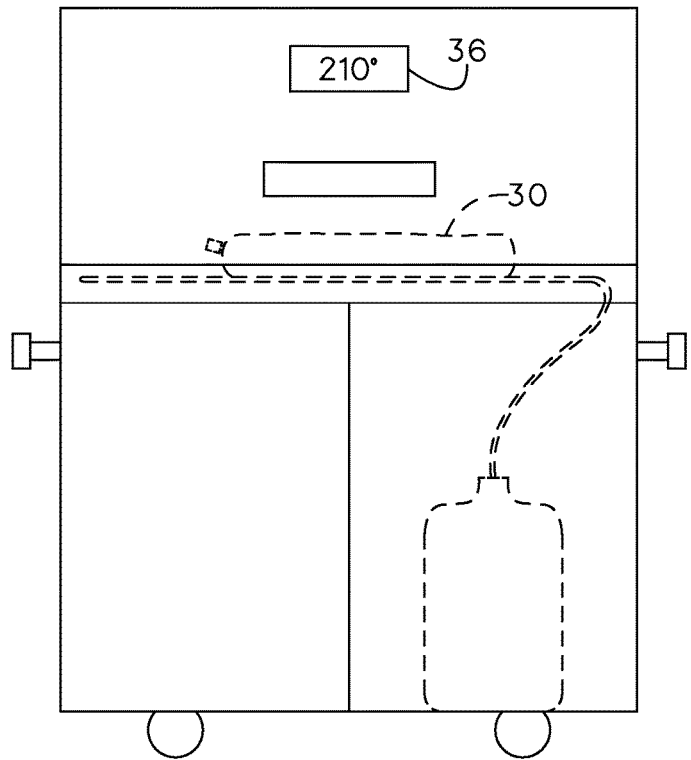
FIG. 6 is a perspective view of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the present invention.

Broadly, an embodiment of the present invention provides a device, system and method for remotely determining the temperature and orientation of at least one medium, such as foodstuff. The device may form a body adapted to penetrate a medium, wherein the body houses a thermal sensor, an accelerometer sensor, a gyroscopic sensor, each electronically connected to a wireless transmitter extending from the body. The plurality of sensors may be adapted to determine the continuous temperature, relative position and orientation of the penetrated medium, all relative to time, while the wireless transmitter is adapted to transmit the plurality such determinations to at least one remote device. The resulting system enables a user to remotely monitoring a level of doneness for a plurality of media in terms of their respective temperatures, orientations, and positioning relative to the time spent on or in at least one heating element.

Referring now to FIGS. 1 through 6, the present invention may include a sensing device 10 embodied a sensing system 100. The sensing device 10 may include a body 12 providing a thermal sensor 16, an accelerometer sensor 18, a gyroscopic sensor 20 and a control circuitry 22 electrically connected to a power source 24 and electronically connected to a wireless transmitter 14. The control circuitry 22 may be adapted to correlate determinations of the thermal sensor 16, the accelerometer sensor 18, and the gyroscopic sensor 20 relative to time. In an alternative embodiment, each such sensor 16, 18, 20 may make time-dependent and relative determinations.

The thermal sensor 16 may be adapted to determine the temperature of a portion of the medium 30 relative to time (located near the thermal sensor 16 of the medium 30 it is embedded in). The accelerometer sensor 18 may be adapted to determine a change in orientation of a portion of the medium 30 relative to time located near the accelerometer sensor 18; for example, the accelerometer sensor 18 may allow one to determine how much time the medium 30 has spent cooking on each side The gyroscopic sensor 20 may be adapted to determine a position relative to time of a portion of the medium 30 relative to time located near the gyroscopic sensor 20; for example, the gyroscopic sensor 20 allows one to determine how much time the medium 30 has spent at a position relative to, say, a heating element.

As a result, the sensors 16, 18, 20 may output regarding the determined internal temperatures, the positions and orientations of the medium, along with time spent in various positions and orientations and at determined temperatures. The wireless transmitter 14 may be adapted to send a plurality of output data provided by the sensors 16, 18, 20.

The body 12 may form a conical shaped end adapted for penetrating a medium 30. The medium 30 may include, but not be limited to, foodstuff. The wireless transmitter 14 may be separated from the body 12 by a bridge 26, such as a threaded fastener, so that the transmitter 14 remains outside the medium 30 whilst the body 12 is substantially embedded therein, as illustrated in FIG. 1.

The sensing system 100 may include the sensing device 10 and a remote device 28. The remote device 28 may include at least one computer with a user interface 40. The computer may include at least one processing unit and a form of memory including, but not limited to, a desktop, laptop, and smart device, such as, a tablet and smart phone. The computer includes a program product including a machine-readable program code for causing, when executed, the computer to perform steps. The program product may include software which may either be loaded onto the computer or accessed by the computer. The loaded software may include an application on a smart device. The software may be accessed by the computer using a web browser. The computer may access the software via the web browser using the internet, extranet, intranet, host server, internet cloud and the like.

The program product may be adapted to simultaneously receive a plurality of output data transmitted from a plurality of wireless transmitters 14. The remote device 28 may be configured to remotely display the plurality of output data, whereby the internal temperature and orientation of the medium 30 can be continuously determined (relative to time) can be determined and displayed on the remote device 28. For example, a user may be able to remotely monitor the length of time a medium 30 is heated (or cooled) undisturbed, how long on each side and/or in each position. The remote device 28 may be adapted to display said plurality of output data to a plurality of display units, including, but not limited to, a pan handle 32, an oven 34, a barbeque grill 36 and the like.

The program product may have a display to alert the user when the medium 30 reaches a predetermined level of "doneness." The level of doneness (el dente) may be defined as obtaining a predetermined temperature, maintaining a predetermined temperature for a predetermined time, being positioned to each predetermined orientation for a predetermine time in each orientation, and the like. The program product may also be adapted to prompt the user to set the type of medium 30 and the level of doneness desired.

The wireless transmitter 14 may be made from heat resistant material and/or be encased therein. The wireless transmitter 14 may be in electronic communication with the remote device 28. Likewise, the body 12 may be made of heat resistant material for insulating for the sensors 16, 18, 20 housed therein.

A method of using the present invention may include the following. A sensing system 100 as described above may be provided. A user may insert the body 12 into the medium 30, for example a slab of meat, until just the wireless transmitter 14 is protruding from the medium 30. The medium 30 is placed on a heating element. The plurality of output data may be wirelessly transmitted from the wireless transmitter 14 to the remote device 28. On the user interface 40 the user would simply click on a numbered icon and select the type and thickness of the meat and the level of doneness to start the tracking of the temperature, orientation and cooking time of the meat. The user interface 40 and/or the display units 32, 34, 36 would display, for example, the internal temperature of the meat as well as how long it has been cooking on each side. Depending on the cut and type of meat, when the meat reaches the predetermined temperature and the user could click again on the icon to track the resting/cooling time of the meat.

The computer-based data processing system and method described above is for purposes of example only, and may be implemented in any type of computer system or programming or processing environment, or in a computer program, alone or in conjunction with hardware. The present invention may also be implemented in software stored on a computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

It should be understood, of course, that the foregoing relates to exemplary embodiments of the invention and that modifications may be made without departing from the spirit and scope of the present invention.

What is claimed is:

1. A device for remotely determining levels of doneness for a medium, comprising:
   a body housing a thermal sensor, an accelerometer sensor, and a control circuitry coupled to said sensors, wherein the body is dimensioned so that said sensors and the control circuitry are disposed entirely in the medium; and
   a wireless transmitter separated from the body so that the wireless transmitter is configured to be disposed outside the medium while said sensors and the control circuitry are disposed entirely in the medium, wherein the wireless transmitter is electronically connected to said sensors so that their determinations are time dependent.

2. The device of claim 1, wherein the body forms a conical shape at one end and the wireless transmitter extends from an opposing end.

3. The device of claim 1, further comprising a bridge interconnecting the wireless transmitter and the body.

4. The device of claim 1, wherein the body is made of heat resistant material.

5. The device of claim 1, further comprising a gyroscopic sensor housed within the body.

6. A device for remotely determining levels of doneness for a medium, comprising:
- a body housing a thermal sensor, an accelerometer sensor, a gyroscopic sensor, and a control circuitry coupled to said sensors, wherein the body is dimensioned so that said sensors and the control circuitry are disposed entirely in the medium, wherein the body is made of heat resistant material formed into a conical shape at one end;
- a wireless transmitter electronically connected to said sensors so that their determinations are time dependent; and
- a bridge interconnecting the wireless transmitter and an end opposing the one end of the body so that the wireless transmitter is disposed outside the medium while said sensors and the control circuitry are disposed entirely in the medium.

7. A method for remotely determining a level of doneness of at least one medium, comprising the steps of:
- providing a device for remotely determining levels of doneness for a medium, comprising:
  - a body housing a thermal sensor, an accelerometer sensor, and a control circuitry coupled to said sensors, wherein the body is dimensioned so that said sensors and the control circuitry are disposed entirely in the medium; and
  - a wireless transmitter separated from one end of the body so that the wireless transmitter is configured to be disposed outside the medium while said sensors and the control circuitry are disposed entirely in the medium, wherein the wireless transmitter is electronically connected to said sensors so that their determinations are time dependent;
- providing a remote device configured to display output data of said sensors relative to time;
- penetrating each medium with the device so that the wireless transmitter protrudes from its penetrated medium; and
- positioning each medium on a heating element.

8. The method of claim 7, further comprising the step of establishing the level of doneness as a function of an orientation of each medium relative to time as determined by the accelerometer sensor.

9. The method of claim 7, further comprising the step of establishing the level of doneness as a function of a predetermined number of re-orientations of each medium, each orientation determined relative to time.

10. The method of claim 7, wherein the body houses an gyroscopic sensor; and further comprising the step of establishing the level of doneness as a function of a position each medium assumes relative to the heating element.

\* \* \* \* \*